United States Patent [19]

Pestellini et al.

[11] Patent Number: 4,800,208
[45] Date of Patent: Jan. 24, 1989

[54] (BENZOFURAN-2-YL)IMIDAZOLES HAVING PHARMACEUTICAL ACTIVITY, THEIR SALTS AND RELEVANT PRODUCTION PROCESSES

[75] Inventors: Vittorio Pestellini; Mario Ghelardoni, both of Florence; Danilo Giannotti, Lucca; Alessandro Giolitti, Florence; Adriano Barzanti, Florence; Rossella Ciappi, Florence; Carlo Ortolani, Riccione, Forli', all of Italy

[73] Assignee: A. Menarini s.a.s., Italy

[21] Appl. No.: 85,067

[22] Filed: Aug. 13, 1987

[30] Foreign Application Priority Data

Aug. 13, 1986 [IT] Italy ............... 9461 A/86

[51] Int. Cl.$^4$ ............... A61K 31/34; A61K 31/415; C07D 403/06
[52] U.S. Cl. ............... 514/397; 548/336
[58] Field of Search ............... 548/336; 514/396, 397

[56] References Cited

U.S. PATENT DOCUMENTS 3,928,348 12/1975 Draber et al. ............... 548/336
4,485,112 11/1984 Pestellini et al. ............... 514/469

*Primary Examiner*—John M. Ford
*Assistant Examiner*—Zinna Northington
*Attorney, Agent, or Firm*—McGlew and Tuttle

[57] ABSTRACT

Compounds corresponding to the general formula

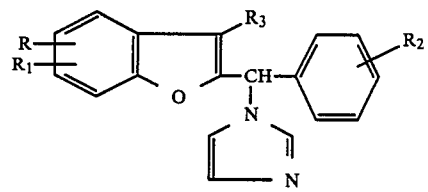

wherein: R and R1, that may be different, represent a hydrogen atom, a halogen, an alkyl group, an alkoxy radical in which the alkyl group contains one to four carbon atoms, a nitro group, a cyano group, an amino group, an acetamino group, a sulfamidic or N-substituted sulfamidic group; R2 represents a hydrogen atom, a halogen, an alkoxy radical, an alkyl group, a phenyl group, a phenylalkyl group, a phenylalkylene or phenylalkenyl group in which the alkylene or alkenyl radical contains two to four carbon atoms, a nitro group, a cyano group, an amino group, an acetamino group, an N-substituted suylfamidic group; and R3 represents a hydrogen atom, an alkyl group, preferably containing one to three carbon atoms or a cyano group.

6 Claims, No Drawings

(BENZOFURAN-2-YL)IMIDAZOLES HAVING PHARMACEUTICAL ACTIVITY, THEIR SALTS AND RELEVANT PRODUCTION PROCESSES

DESCRIPTION

The present invention relates to new benzofuran-2-yl-imidazole derivatives having a broad spectrum of antifungal activity, corresponding to general formula I, and to their salts obtained by pharmaceutically acceptable acids:

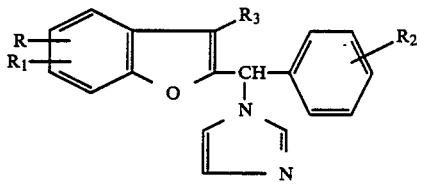

wherein:

R and R1, that may be different between them, represent a hydrogen atom, a halogen, preferably chlorine or bromine, an alkyl group, preferably containing one to four carbon atoms, an alkoxy radical in which the alkyl group contains one to four carbon atoms, a nitro group, a cyano group, an amino group, an acetamino group, a sulfamidic or N-substituted sulfamidic group;

R2 represents a hydrogen atom, a halogen, an alkoxy radical, in which the alkyl group contains one to four carbon atoms, an alkyl group, preferably containing one to four carbon atoms, a phenyl, group, a phenylalkyl group, such as benzyl, a phenylalkylene or phenylalkenyl group in which the alkylene or alkenyl radical contains two to four carbon atoms, a nitro group, a cyano group, an amino group, an acetamino group, a sulfamidic or N-substituted sulfamidic group;

R3 represents a hydrogen atom, an alkyl group, preferably containing one to three carbon atoms or a cyano group.

Pharmaceutically acceptable salts are, in particular, those having lower toxicity and which are commonly used in the pharmaceutical practice, such as for example those obtained by hydrochloric acid, phosphoric acid, mono or bifunctional carboxylic acids, such as for example acetic acid, propionic acid, maleic acid, succinic acid, fumaric acid, tartaric acid, citric acid, salicylic acid, lactic acid.

Compounds of the general formula I can be obtained from compounds of the general formula II

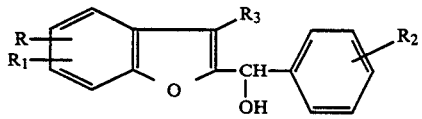

wherein, R, R1, R2 and R3 are as above defined, directly through a treatment with thionylbisimidazole having formula:

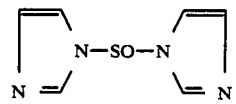

or through a treatment with 1,1-carbonyldiimidazole having formula:

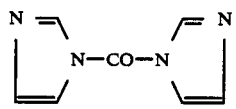

or may be obtained through a treatment with free or salified imidazole, from the halogen derivatives of general formula III

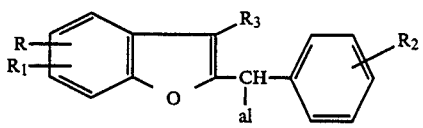

wherein R, R1, R2 and R3 are as above defined and "al" indicates halogen.

Non limitative examples of compounds of general formula II are: (benzofuran-2-yl)(p-chlorophenyl)methanol, (5,7-dichlorobenzofuran-2-yl)(p-chlorophenyl)methanol, (benzofuran-2-yl)phenylmethanol, (5-nitrobenzofuran-2-yl)phenyl-methanol, (benzofuran-2-yl)(p-methylphenyl)methanol, (benzofuran-2-yl)(o-chlorophenyl)methanol, (5-chlorobenzofuran-2-yl)phenylmethanol, (benzofuran-2-yl)(p-fluorphenyl)methanol, (benzofuran-2-yl)(p-biphenylyl)methanol, (benzofuran-2-yl)(o-methylphenyl)methanol, (5,7-dichlorobenzofuran-2-yl)phenyl methanol, (5-bromobenzofuran-2-yl)phenylmethanol, (benzofuran-2-yl)(stilben-4-yl)methanol, (benzofuran-2-yl)(o-metoxyphenyl)methanol, (5-chlorobenzofuran-2-yl)(o-chlorophenyl)methanol, (benzofuran-2-yl)(p-nitrophenyl)methanol, (5-bromobenzofuran-2-yl)(p-chlorophenyl)methanol, (5-bromobenzofuran-2yl)(o-chlorophenyl)methanol, (3-methylbenzofuran-2-yl)phenyl-methanol, (7-methoxy-benzofuran-2-yl)(o-chlorophenyl)-methanol, (5-methyl-benzofuran-2-yl)(o-chlorophenyl)-methanol.

These starting compounds, when subjected to the treatment with thionylbisimidazole or with carbonyldiimidazole, afford the corresponding imidazole derivatives of general formula I.

The reaction is usually carried out by using two moles of thionylbisimidazole or carbonyldiimidazole for each mole of utilized starting material, by operating in an organic solvent, like for example acetone, acetonitrile, dioxane, chloroform: said reaction is generally carried out in the presence of a base as for example alkaline carbonates, tertiary alkyl amines, pyridine.

The raw product resulting from the above reaction is suitably purified by crystallization or by transforming it into the corresponding acid salt from which the free base is restored by a treatment with alkalis.

According to the method of the present invention, the starting materials of general formula II may also be transformed into the corresponding imidazol derivatives of general formula I, through a treatment with halogenating agents, so as to replace the hydroxyl group with a halogen and through a successive treatment of the halogen-intermediate thus obtained, with free or salified imidazole.

Non limitative examples of intermediate halogen-derivatives of general formula III, are: (benzofuran-2-yl)(p-chlorophenyl)methylbromide, (5,7-dichlorobenzofuran-2-yl)(p-chlorophenyl)methylchloride, (benzofuran-2-yl)phenyl-methyl chloride, (5-nitrobenzofuran-2-yl)phenyl-methyl-chloride, (benzofuran-2-yl)(p-methylphenyl)methyl chloride, (benzofuran-2-yl)(o-chlorophenyl)methylchloride, (5-chlorobenzofuran-2-yl)phenylmethylchloride, (benzofuran-2-yl)(p-fluorophenyl)methylchloride, (benzofuran-2-yl)(p-biphenylyl)methylchloride, (benzofuran-2-yl)(o-methylphenyl)methylbromide, (5,7-dichlorobenzofuran-2-yl)phenylmethylchloride, (5-bromobenzofuran-2-yl)phenylmethylchloride, (benzofuran-2-yl)(stilben-4-yl)methylchloride, (benzofuran-2-yl)(o-metoxyphenyl)methylchloride, (5-chlorobenzofuran-2-yl)(o-chlorophenyl)methylchloride, (benzofuran-2yl)(p-nitrophenyl)methylchloride, (5-bromobenzofuran-2-yl)(p-chlorophenyl)methylchloride), (5-bromobenzofuran-2-yl)(o-chlorophenyl)methylchloride, (5-methyl-benzofuran-2-yl)(o-chlorophenyl)methylchloride.

This reaction is usually carried out in polar solvents, as for example nitriles, dimethylsulfoxide, acetone or ethers, as well as ethylether or dioxane, chlorohydrocarbons, such as chloroform or methylene chloride. The product thus obtained is usually taken up again by distillation of the solvent. The raw product is suitably purified as above mentioned.

The starting materials of general formula II are generally known or, should they not be already disclosed in the literature, they may be easily prepared from the ketones which, for the sake of simplicity, are indicated in the general formula IV

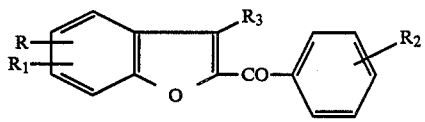

wherein R, R1, R2 and R3 are as above defined, through classic reduction methods, such as for example a treatment with sodium borohydride or through a treatment with isopropyl aluminium.

Also the ketones of general formula IV are generally known; in case they are not disclosed in the literature, they can be easily prepared through the classic methods, such as for example by treating the suitable salicylaldehyde with the substituted ω-bromoacetophenone.

Some non limitative examples of derivative compounds of general formula I are given below:

1. 1-[(benzofuran-2-yl)(p-chloro-phenyl)methyl]-1H-imidazole hydrochloride
(Form. I R=R1=R3=H R2=4-Cl)
m.p. 187°–189° C.

2. 1-[(5,7-dichlorobenzofuran-2-yl)(p-chlorophenyl)methyl]-1H-imidazole hydrochloride
(Form. I R=R1=Cl R2=4-Cl R3=H)

3. 1-[(benzofuran-2-yl)phenylmethyl]-1H-imidazole hydrochloride
(Form. I R=R1=R2=R3=H) m.p. 205°–207° C. (dec.).

4. 1-[(5-nitrobenzofuran-2-yl)phenylmethyl]-1H-imidazole hydrochloride
(Form. I R=5NO2 R1=R2 R3=H)
m.p. 168°–170° C.

5. 1-[(benzofuran-2-yl)(p-methylphenyl)methyl]-1H-imidazole hydrochloride
(Form. I R=R1=R3=H R2=4-CH3)
m.p. 185°–186° C.

6. 1-[(benzofuran-2-yl)(o-chlorophenyl)methyl]-1H-imidazole hydrochloride
(Form. I R=R1=R3=H R2=2-Cl)
m.p. 179°–181° C.

7. 1-[(5-chlorobenzofuran-2-yl)phenylmethyl]-1H-imidazole hydrochloride
(Form. I R=5-Cl R1=R2=R3=H)
m.p. 181°–182° C.

8. 1-[(benzofuran-2-yl)(p-fluorphenyl)methyl]-1H-imidazole hydrochloride
(Form. I R=R1=R3=H R2=4-F)
m.p. 181°–182° C.

9. 1-[(benzofuran-2-yl)(p-biphenylyl)methyl]-1H-imidazole hydrochloride
(Form. I R=R1=R3=H R2=C6H5)
m.p. 130°–133° C. (dec.).

10. 1-[(benzofuran-2-yl)(o-methylphenyl)methyl]-1H-imidazole hydrochloride
(Form. I R=R1=R3=H R2=2-CH3)
m.p. 177°–178° C.

11. 1-[(5,7-dichlorobenzofuran-2-yl)phenylmethyl]-1H-imidazole hydrochloride
(Form. I R=R1=Cl R2=R3=H)

12. 1-[(5-bromobenzofuran-2-yl)phenylmethyl]-1H-imidazole hydrochloride
(Form. I R=5-Br R1=R2=R3=H)
m.p. 173°–174° C.

13. 1-[(benzofuran-2-yl)(stilben-4-yl)methyl]-1H-imidazole
(Form. I R=R1=R3=H R2=CH=CH—C6H5)
m.p. 145°–148° C. (dec.).

14. 1-[(benzofuran-2-yl)(o-methoxyphenyl)methyl]-1H-imidazole hydrochloride
(Form. I R=R1=R3=H R2=2-OCH3)
m.p. 175°–177° C.

15. 1-[(5-chlorobenzofuran-2-yl)(o-chlorophenyl)methyl]-1H-imidazole hydrochloride
(Form. I R=5-Cl R1=R3=H R2=2-Cl)
m.p. 178°–180° C.

16. 1-[(benzofuran-2-yl)(p-nitrphenyl)methyl]-1H-imidazole hydrochloride
(Form. I R=R1=R3=H R2=4-NO2)
m.p. 138°–140° C.

17. 1-[(3-methylbenzofuran-2-yl)phenylmethyl]-1H-imidazole
(Form. I R=R1=R2=H R3=CH3)
m.p. 154°–155° C.

18. 1-[(7-(methoxybenzofuran-2-yl)(o-chlorophenyl)methyl]-1H-imidazole hydrochloride
(Form. I R=7-OCH3 R1=R3=H R2=2-Cl)
m.p. 143°–146° C. (dec.).

19. 1-[(5-methylbenzofuran-2-yl)(o-chlorophenyl)methyl]-1H-imidazole hydrochloride
(Form. I R=5-CH3 R1=R3=H R2=2-Cl)
m.p. 167°–169° C.

20. 1-[(5-bromobenzofuran-2-yl)(o-chlorophenyl)methyl]-1H-imidazole
(Form. I R=5-Br R1=R3=H R2=2-Cl)
m.p. 78°–81° C.

21. 1-[(5-chlorobenzofuran-2-yl)(2,5-dichlorophenyl)methyl]-1H-imidazole hydrochloride
(Form. I R=5Cl R1=R3=H R2=2,5Cl)

m.p. 135°–138° C. (dec.).

The (benzofuran-2-yl)-phenylmethyl imidazoles of the general formula I and their pharmaceutically acceptable salts have pharmacologic activities that make them commercially useful. In particular, they have a marked antifungal and antibacterial action and, owing to their low toxicity, they are useful as mycostats, especially in regard to etiologic agents of vaginal mycosis, visceral mycosis (pulmonary, renal, generalized endocardial) and in the treatment of immunodepressed persons.

The compounds of the present invention are suitable for oral, parenteral, as well as topical administration in the form of tablets, pills, powders, granules, syrups, pastes, ointments, gels, sprays, lotions, suspensions and injectable solutions.

In the pharmaceutical formulations suitable for the administration, the compounds of the present invention are in an amount ranging between 0.1 and 30%, preferably between 0.5 and 10% by weight, in a admixture with the usual excipients or inert carriers such as for example: gelating agents, bases for suppositories, auxiliary products for tablets or other excipients for the active ingredients, as for example antioxidants, dispersing agents, emulsifiers, antifoam agents, taste correctors, preservatives, solubilizing and colouring agents.

It is advisable to administer the active compounds in one or more daily doses in the range between 0.5 and 100 mg/kg of body weight, preferably from 1 to 30 mg/kg of body weight.

The optimal dosage and the administration method of the active compounds to be used in every particular case are easily determined by any expert according to his experience.

Included in the present invention are pharmaceutical formulations making up associations of one or more compounds, according to the present invention, which can be associated with one or more pharmaceutically active compounds belonging to other groups of medicines, as e.g. local anesthetic and antibacterial medicines.

Some examples indicating the preparation methods, the exhibited activity and the relevant pharmaceutical formulations of the compounds according to the invention are given below:

EXAMPLE 1

1-[(5-bromobenzofuran-2-yl)phenyl methyl]-1H-imidazole hydrochloride

To 11.9 g of imidazole in 250 ml of dioxane, at the reflux temperature under strong agitation, 28.1 g of (5-bromobenzofuran-2-yl)phenyl methylchloride are added drop by drop in 200 ml of dioxane keeping on with the reflux for further 5 hours, then cooling up, filtering out and bringing the mother waters to dryness. The residue is taken up again with ethylether, washed first with 2% sodium hydrate solution and then with water: from the ethereal solutions the compound is extracted by means of a solution of 5% hydrochloric acid and then, by alkalinization with 5% NaOH, an oil is obtained with is extracted again with ethylether. The ethereal extract is washed, rendered anhydrous and brought to dryness to afford a solid which crystallizes from isopropanol: m.p. 123°–124° C.

The product is dissolved in ethyl acetate, then gaseous HCl is delivered affording a precipitate: m.p. 173°–174° C. (acetone).

EXAMPLE 2

1-[(5-chlorobenzofuran-2-yl)(o-chlorophenyl)methyl]-1H-imidazole hydrochloride

To 0.2 moles of imidazole in 200 ml of dioxane, 0.07 moles of (5-chlorobenzofuran-2-yl)(o-chlorophenyl)-methyl chloride in 10 ml of dioxane are slowly added under agitation at the boiling point temperature: after a further 5 hour falling time, the admixture is cooled and filtered out and the mother liquors are brought to dryness under vacuum condition. The oil thus obtained is taken up with ethylether, washed with 2% NaOH solution, with water, and then extracted by a 5% HCl solution. An alkalinization with 5% NaOH follows which gives rise to a precipitate that is again extracted with ether and the solution saturated with gaseous HCl; the precipitate thus obtained is crystallized from acetone: m.p. 178°–80° C.

By dissolving the hydrochloride in water and alkalinizing with bicarbonate, an oil is obtained which is extracted with ethylether: the solution is made anhydrous, brought to dryness and the base is crystallized from hexane: m.p. 78°–80° C. (dec.).

EXAMPLE 3

1-[(benzofuran-2-yl)phenylmethyl]-1H-imidazole-hydrochloride

To 0.08 moles of imidazole in 70 ml of acetonitrile, at the temperature of 10 C., 0.02 moles of thionylchloride are added, followed by 1 hour rest, and then 0.02 moles of (benzofuran-2-yl)phenylmethanol are added in 20 ml of acetonitrile. The reaction admixture is kept 24 hours at ambient temperature and then concentrated to dryness. The residue is taken up with ethylether, washed first with 2% sodium hydrate solution and then with water: the hydrochloride is obtained from the ethereal solutions using 5% hydrochloric acid, then an oil is obtained by alkalinization with 5% NaOH, which is extracted with ethylether. The ethereal extract is washed, made anhydrous and saturated with gaseous HCl: the precipitate thus obtained is crystallized from isopropanol: m.p. 205°–207° C. (dec.).

EXAMPLE 4

(5-bromobenzofuran-2-yl)(p-chlorophenyl)methylchloride

To 36.2 g of (5-bromobenzofuran-2-yl)(p-chlorophenyl)methanol dissolved in 50 ml of methylenchloride, 8.5 ml of thionylchloride in 25 ml of cyclohexane are added drop by drop, under agitation. After a 4 hour rest at 10° C., the solution is brought to dryness under vacuum condition. The residue is crystallized from petroleum ether: m.p. 83°–85° C.

EXAMPLE 5

(5,7-dichlorobenzofuran-2-yl)(p-chlorophenyl)methylchloride

To 0.35 mole of thionylchloride in 300 ml of cyclohexane, 0.31 mole of (5,7-dichlorobenzofuran-2-yl)(p-chlorophenyl)carbinol are portions-like added followed by 3-hour agitation at ambient temperature; then the solution is concentrated, filtered out and crystallized from cyclohexane: m.p. 72°–74° C.

Biological activity: by using such culture media as, respectively, Sabouraud pH7 and Mycological Broth pH7, the Minimum Inhibiting Concentrations (MIC)

have been computed after dissolution of the compounds having general formula I into dimethylsulfoxide: the data obtained are generally equal to or better than that from the comparison products (bifonazole, griseofulvin): the compounds of the present patent have shown to be particularly active to yeasts, such as for example *Torulopsis glabrata, Rhodotorula flava, Cryptococcus neoformans;* over several dermathophytes, such as for example *Microsporum canis, Microsporum gypseum,* as well as over other mycetes, such as for example *Penicillium lilacinum, Geotrichum candidum, Penicillium funicolosum.*

The compounds have also an antibacterial action: the 50% MIC relevant to bacteria such as *S. aureus* and *P. aeuriginosa* fall between 0.25 and 1 γ/ml.

The following pharmaceutical formulation is given as a non limitative example.

EXAMPLE 6

Preparation of a Paste 1 g of the compound of general formula I is solubilized (or dispersed) at a temperaure of about 70°–75° C., under agitation, into 2 g of monopalmitate sorbitan, 3 g of spermaceti, 10 g cetylstearic acid, 13.5 g of octyldodecanol and 1 g of benzylic alcohol.

To this solution (suspension), still under strong agitation, 69 g of water already warmed up at 70°–75° C. are added.

Once the addition of water is completed, the paste is vacuum-deaerated and brought to ambient temperature.

We claim:

1. A compound corresponding to the formula

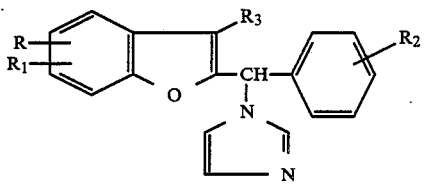

wherein:

R and $R_1$, which may be the same or different, represent a hydrogen atom, a halogen atom, an alkyl group, an alkoxy group having one to four carbon atoms, a nitro group, a cyano group, an amino group, or an acetamino group, $R_2$ represents a hydrogen atom, a halogen atom, an alkyl group, an alkoxy group having one to four carbon atoms, a phenyl group, a phenylalkyl group, a phenylalkenyl group in which the alkenyl radical has two to four carbon atoms, a nitro group, a cyano group, an amino group, or an acetamino group, and $R_3$ represents a hydrogen atom, an alkyl group having one to three carbon atoms, or a cyano group, alkyl unless otherwise specified having one to four carbon atoms or a salt thereof.

2. A compound of claim 1 wherein the salt is a non-toxic, pharmaceutically acceptable salt of an organic or inorganic acid.

3. A compound of claim 1 wherein

R and $R_1$, which may be the same or different, represent a hydrogen atom, a chlorine atom, a bromine atom, an alkyl group having one to four carbon atoms, an alkoxy group having one to four carbon atoms, a nitro group, a cyano group, an amino group, or an acetamino group;

$R_2$ represents a hydrogen atom, a halogen atom, an alkyl group having one to four carbon atoms, an alkoxy group having one to four carbon atoms, a phenyl group, a benzyl group, a phenylalkenyl group in which the alkenyl radical has two to four carbon atoms, a nitro group, a cyano group, an amino group, or an acetamino group; and $R_3$ represents a hydrogen atom, an alkyl group having one to three carbon atoms, or a cyano group.

4. A compound selected from the group consisting of:
(1) 1-[(benzofuran-2-yl)(p-chlorophenyl)methyl]-1H-imidazole or a salt thereof,
(2) 1-[(5,7-dichlorobenzofuran-2-yl)(p-chlorophenyl)methyl]-1H-imidazole or a salt thereof,
(3) 1-[(benzofuran-2-yl)(phenyl)methyl]-1H-imidazole or a salt thereof,
(4) 1-[(5-nitrobenzofuran-2-yl)(phenyl)methyl]-1H-imidazole or a salt thereof,
(5) 1-[(benzofuran-2-yl)(p-methylphenyl)methyl]-1H-imidazole or a salt thereof,
(6) 1-[(benzofuran-2-yl)(o-chlorophenyl)methyl]-1H-imidazole or a salt thereof,
(7) 1-[(5-chlorobenzofuran-2-yl)(phenyl)methyl]-1H-imidazole or a salt thereof,
(8) 1-[(benzofuran-2-yl)(p-fluorophenyl)methyl]-1H-imidazole or a salt thereof,
(9) 1-[(benzofuran-2-yl)(p-biphenylyl)methyl]-1H-imidazole or a salt thereof,
(10) 1-[(benzofuran-2-yl)(o-methylphenyl)methyl]-1H-imidazole or a salt thereof,
(11) 1-[(5,7-dichlorobenzofuran-2-yl)(phenyl)methyl]-1H-imidazole or a salt thereof,
(12) 1-[(5-bromobenzofuran-2-yl)(phenyl)methyl]-1H-imidazole or a salt thereof,
(13) 1-[(benzofuran-2-yl)(stilben-4-yl)methyl]-1H-imidazole or a salt thereof,
(14) 1-[(benzofuran-2-yl)(o-methoxyphenyl)methyl]-1H-imidazole or a salt thereof,
(15) 1-[(5-chlorobenzofuran-2-yl)(o-chlorophenyl)methyl]-1H-imidazole or a salt thereof,
(16) 1-[(benzofuran-2-yl)(p-nitrophenyl)methyl]-1H-imidazole or a salt thereof,
(17) 1-[(3-methylbenzofuran-2-yl)(phenyl)methyl]-1H-imidazole or a salt thereof,
(18) 1-[(7-methoxybenzofuran-2-yl)(o-chlorophenyl)methyl]-1H-imidazole or a salt thereof,
(19) 1-[(5-methoxybenzofuran-2-yl)(o-chlorophenyl)methyl]-1H-imidazole or a salt thereof,
(20) 1-[(5-bromobenzofuran-2-yl)(o-chlorophenyl)methyl-1H-imidazole or a salt thereof, and
(21) 1-[(5-chlorobenzofuran-2-yl)(2,5-dichlorophenyl)methyl]-1H-imidazole or a salt thereof.

5. Antifungal or antibacterial pharmaceutical composition comprising an effective amount of at least one compound of claim 1 as active ingredient in combination with an inert carrier.

6. Antifungal or antibacterial pharmaceutical composition, comprising an effective amount of at least one compound corresponding to the formula

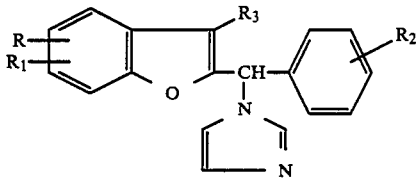

wherein:

R and $R_1$, which may be the same or different, represent a hydrogen atom, a halogen atom, an alkyl group, an alkoxy group having one to four carbon atoms, a nitro group, a cyano group, an amino group, or an acetamino group, $R_2$ represents a hydrogen atom, a halogen atom, an alkyl group, an alkoxy group having one to four carbon atoms, a phenyl group, a phenylalkyl group, a phenylalkenyl group in which the alkenyl radical has two to four carbon atoms, a nitro group, a cyano group, an amino group, or an acetamino group, and $R_3$ represents a hydrogen atom, an alkyl group having one to three carbon atoms, or a cyano group, alkyl unless otherwise specified having one to four carbon atoms or a pharmaceutically acceptable salt thereof, as active ingredient, in combination with an inert carrier, in suitable form for administration by a method selected from the group consisting of oral, parenteral and topical administration.

* * * * *